US00PP09856P

United States Patent [19]

van Geest

[11] Patent Number: Plant 9,856

[45] Date of Patent: Apr. 8, 1997

[54] FICUS VARIETY NAMED 'MIDNIGHT'

[75] Inventor: Jan van Geest, JP's Gravenzande, Netherlands

[73] Assignee: The Plantenkwekerij J. van Geest, B.V., Netherlands

[21] Appl. No.: 507,751

[22] Filed: Jul. 26, 1995

[51] Int. Cl.[6] ..... A01H 5/00

[52] U.S. Cl. ..... Plt./88.9

[58] Field of Search ..... Plt./88.9

[56] References Cited

PUBLICATIONS

Bailey, L.H., et al., "Ficus Benjamina L." *Hortus Third* Macmillan Publishing Co. N.Y. 1976 p. 477.

*Primary Examiner*—James R. Feyrer

*Attorney, Agent, or Firm*—Christie, Parker & Hale, LLP

[57] ABSTRACT

A Ficus variety having compact growth habit and dark green foliage.

3 Drawing Sheets

BACKGROUND OF THE INVENTION

The present invention relates to a new and distinct cultivar of *Ficus benjamina* 'Exotica.' The varietal denomination of the new cultivar is 'Midnight'.

The new variety was discovered as a mutation in a controlled planting of *Ficus benjamina* 'Exotica' in a greenhouse in The Netherlands.

SUMMARY OF THE INVENTION

The new variety is a mutation of the variety *Ficus benjamina* 'Exotica.' Ficus 'Midnight' has been asexually reproduced by rooted cuttings in the Westlands, the Netherlands. Asexual reproduction through succeeding generations has established that the combination of characteristics as herein disclosed for the new cultivar are firmly fixed and retained through successive generations of asexual reproduction.

Comparison with Parent and Other Varieties

Ficus 'Midnight' differs significantly in appearance from its parent Ficus benjamina 'Exotica' in that the color of the leaf blades of the new variety are much darker green in color. 'Exotica' grown under the same conditions as 'Midnight' is much lighter green. The leaf blade color of 'Midnight' is similar to the color of the leaf blades of Ficus 'Indigo'; however, whereas 'Indigo' has a lighter green, irregularly shaped section on its mature foliage, this section is absent on mature foliage of Ficus 'Midnight.'

The new variety is also different from *Ficus benjamina* 'Exotica' in having thicker and crisper leaves. It has also been observed that when 'Midnight' is maintained under low light levels, e.g. less than about 3000 foot candles, it remains extremely durable and capable of holding its foliage, and is highly resistant to leaf drop. Ficus 'Midnight' has a more compact growth pattern than that of Ficus 'Indigo' and 'Exotica' with internode spacing of approximately 13 mm to 20 mm. Internode spacing of 'Indigo' and 'Exotica' grown under the same conditions tend to have internode spacing of about 20 mm to 30mm. The leaves of 'Midnight' are thick, glossy and leathery and an attractive dark green, almost blue-black, without variegation on the leaves.

BRIEF DESCRIPTION OF THE ILLUSTRATION

The accompanying illustrations show a specimen of the new cultivar in photo illustrations as true to color as is reasonably possible to make in an illustration of this character, with one illustration showing the growth habit and the other illustration showing the foliage. Phenotypic expression may vary depending on light, environmental and cultural conditions.

An additional illustration is a comparison of plants of 'Midnight' (on the left) and 'Exotica' (on the right). These specimens were grown under identical conditions under shade (73% shadecloth) in Homestead, Fla. They were planted at the same time as starter plants propagated by vegetative cuttings and each plant contains 6' cuttings per pot. The photograph was taken with shaded natural light conditions.

DESCRIPTION OF THE NEW VARIETY

'Midnight' has not been observed under all possible environmental conditions. The phenotypic expression may vary with variations in environment such as temperature, light intensity, day length and cultural conditions.

The following observations and descriptions are of plants grown in under glass in the Netherlands. In this description, color references are to The Royal Horticultural Society Colour Chart (RHSCC). The terminology used in the color descriptions herein refers to plate numbers in this color chart.

Classification:

*Botanical.*—*Ficus benjamina* 'Midnight'.

Parentage: Mutation of *Ficus benjamina* 'Exotica'.

Propagation: By vegetative cuttings and other known asexual reproduction techniques.

Plant

A. Form: Compact, upwardly branching, ascending, somewhat irregular and richly branching.

B. Growth: Lateral branches tend to be at sharp right angles to the trunk, but slightly weeping at top.

1. *Height Attained.*—Extremely vigorous, about 1.5 to 3 meters.

C. Foliage:

1. *Size.*—About 4 cm wide by about 11 cm long (to leaf tip).
2. *Quantity.*—Multiple, numerous.
3. *Color.*—New foliage: Upper side—near 137B; Underside—near 137B. Old foliage: Upper side—near 131A; Underside—near 139A to 139B.
4. *Shape.*—Ovate with acuminate leaf tip, slightly coarsely sinuate and glabrous.

5. *Texture.*—Smooth, leathery, glossy, slightly thick; underside smooth, matte.
6. *Veination.*—Single mid-rib vein running from petiole to leaftip, convex on the underside, light green, near 145D.
7. *Edge.*—Smooth, slightly undulated.
8. *Serration.*—None.
9. *Stipules.*—Leaves are glabrous.
10. *Auricle.*—Absent.
11. *Petiole.*—Near 144A; about 18 mm long.
12. *Resistance to disease.*—Resistant to anthracnose, agrobacterium radiobacter, tumefaciens, heterodera fici.
13. Rachis.—None.

D. Wood:

1. *New shoots.*—Color—near 197B; smooth.
2. *Old wood.*—Color near 199A; smooth, caliper of the wood does not differ significantly from that of 'Exotica'. Note: To date, and under conditions described herein, the new variety has not borne flowers or fruit.
3. *Temperature range.*—To 2° C.
4. *Internode spacing.*—About 20 to 30 mm.
5. *Preferred Growing Conditions.*—20° C. to 32° C.
6. *Reproductive organs.*—Not observed.

I claim:

1. A new and distinct cultivar of *Ficus benjamina* plant named 'Midnight', substantially as illustrated and described, particularly characterized by dark green foliage and compact growth habit.

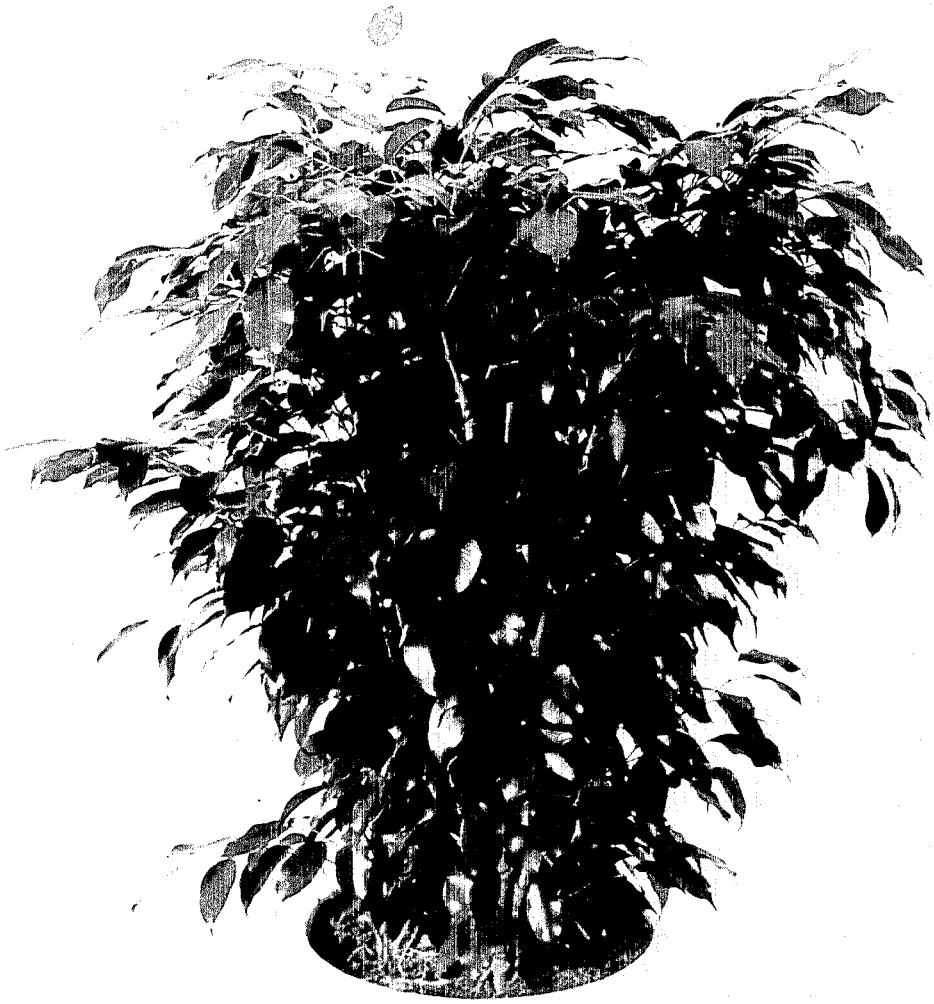

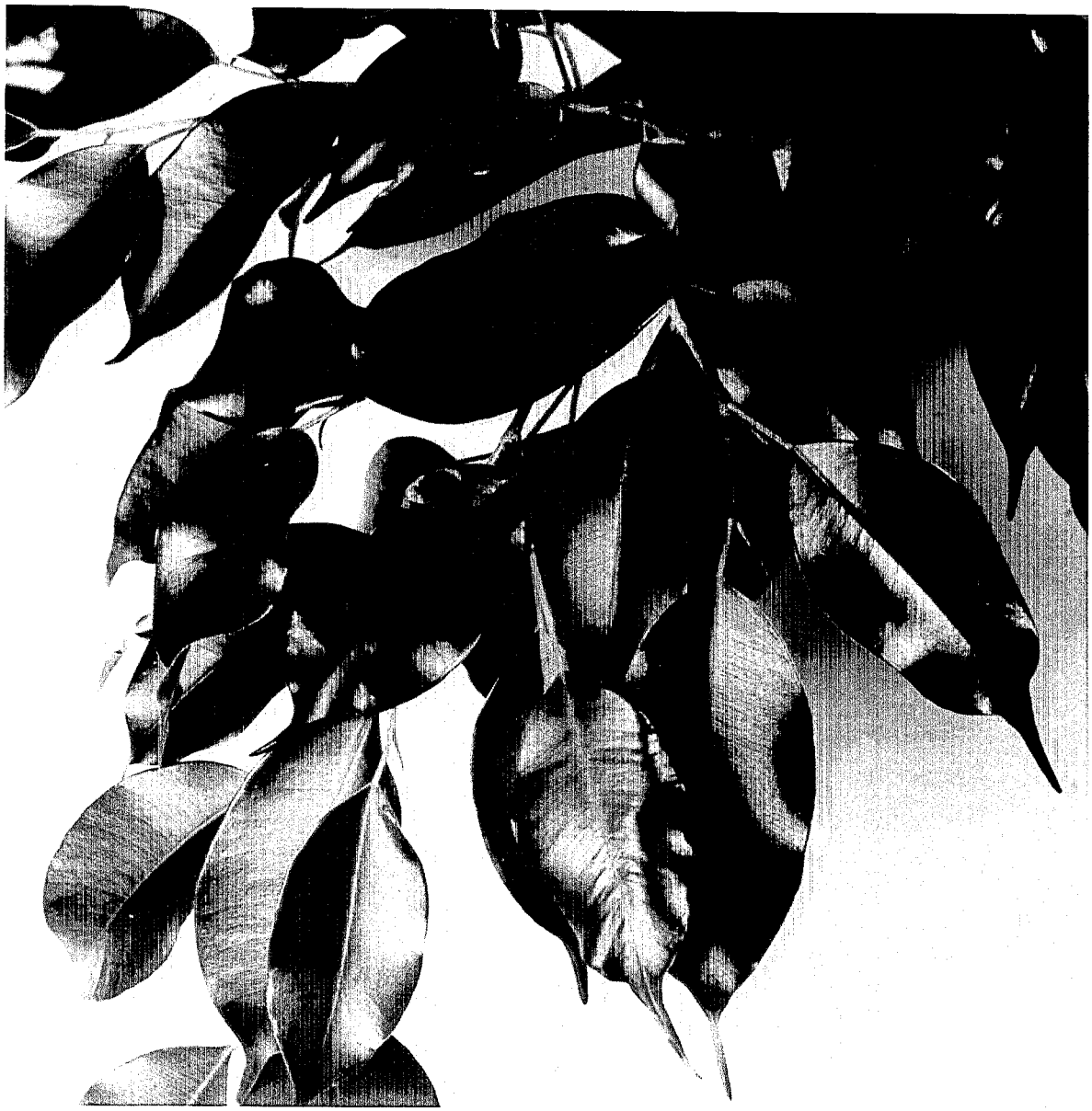

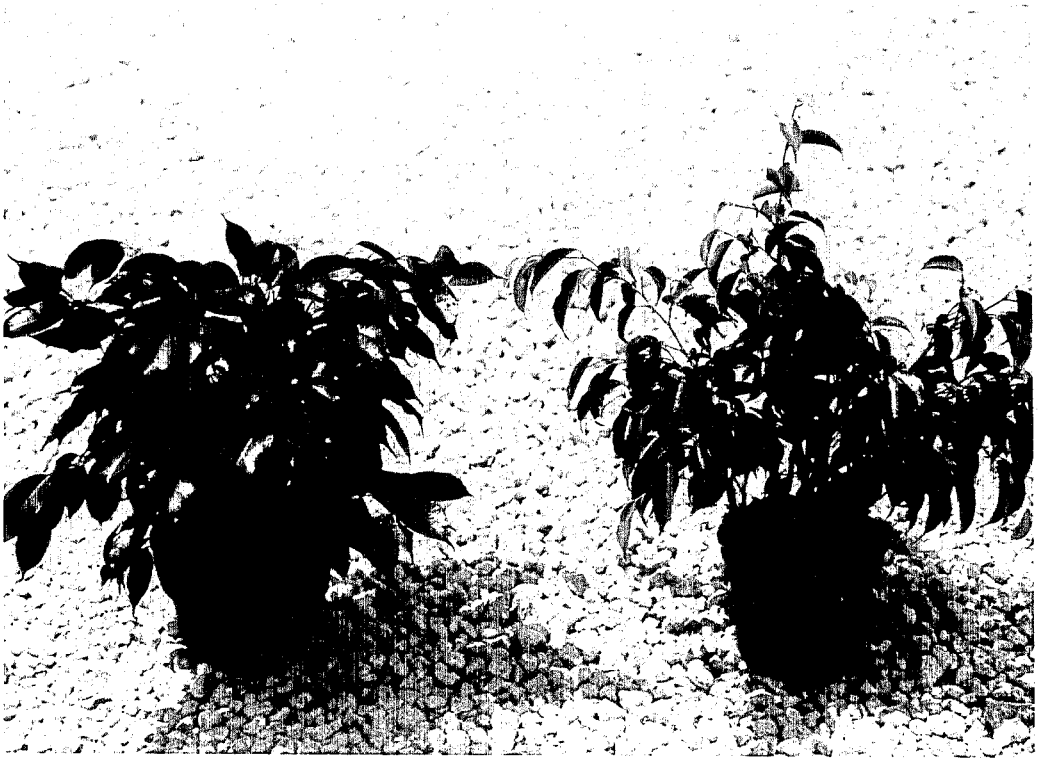

* * * * *